United States Patent
Padmawar

(10) Patent No.: US 7,892,580 B2
(45) Date of Patent: Feb. 22, 2011

(54) PROCESS FOR PRODUCING A STABLE CONCENTRATED DIETARY SUPPLEMENT AND SUPPLEMENT PRODUCED THEREBY

(75) Inventor: Achyut Padmawar, Indore (IN)

(73) Assignee: Nutraceuticals International LLC, Elmwood, NJ (US)

( * ) Notice: Subject to any disclaimer, the term of this patent is extended or adjusted under 35 U.S.C. 154(b) by 27 days.

(21) Appl. No.: 12/433,663

(22) Filed: Apr. 30, 2009

(65) Prior Publication Data

US 2009/0324637 A1 Dec. 31, 2009

Related U.S. Application Data

(60) Provisional application No. 61/049,615, filed on May 1, 2008.

(51) Int. Cl.
*A01N 65/00* (2009.01)
(52) U.S. Cl. .................................................... 424/725
(58) Field of Classification Search ....................... None See application file for complete search history.

(56) References Cited

U.S. PATENT DOCUMENTS

2007/0036742 A1* 2/2007 Roufs et al. ................... 424/74

* cited by examiner

*Primary Examiner*—Michael V Meller
(74) *Attorney, Agent, or Firm*—Ostrolenk Faber LLP

(57) ABSTRACT

A process for producing a stable concentrated dietary supplement containing fucoxanthin as the main active component. The method entails grinding crude freeze-dried flakes of wakame seaweed (*Undaria pinnatifida*) with desirable characteristics into a powder, extracting the active fucoxanthin from the powder with use of an aliphatic or aromatic organic solvent, then filtering and distilling the extract to form a thick syrupy fucoxanthin-containing mass having a solids content of from about 10-99% by wt. The mass is then purified by dissolving it in an organic non-polar solvent having a Polarity Index of <6, wherein the resultant solution is filtered to remove any solid material therefrom and the remaining liquid is then concentrated to a dried mass by removing substantially all of the solvent, which mass is thereafter ground and sifted to obtain a plurality of particles measuring approximately 60-100 mesh in size. The particles contain at least about 10% by weight of fucoxanthin. The particles by themselves, or in admixture with other components well known in the relevant art, thus comprise a supplement which may be constituted in a form selected from, for example, tablets, capsules, powders and granules.

12 Claims, 2 Drawing Sheets

FIGURE 1

PROCESS FLOW CHART

Crude wakame flakes comprising >0.5 wt% fucoxanthin are ground to a powder (e.g., 10-20 mesh size) with a pulverizer.

↓

The pulverized material is analyzed by a batch analysis process with regard to the QC parameters given in Table 1 (Fig. 2). After QC approval, the material is subject to an extraction treatment as set forth below.

↓

Extraction: Preferably 100 Kg of the material is loaded into an extractor and 500 liters of an aliphatic or aromatic organic solvent (e.g., ethanol of 80-95% purity) is added thereto. The extraction may be carried out at 10-70°C for approx. 3 hours with continuous circulating solvent. After completion, the solvent phase is filtered and the liquid is transferred to a distillation apparatus. The extraction cycle may be repeated up to 5 times and the extracts combined for further treatment.

↓

Distillation: Distillation of the solvent phase is carried out under reduced pressure below 50°C to produce a thick syrupy mass having a solids content of 10-99% by weight.

↓

The mass is dissolved in an organic non-polar solvent having a polarity index <6 (e.g., ethyl acetate) and the insoluble portion is discarded. The filtrate is again concentrated, analyzed for heavy metals and iodine and dried, e.g., in a vacuum rotary drier at a temperature below 50°C.

↓

The dried mass is ground, sifted and analyzed for the parameters given in Table 2 (Fig. 2).

FIGURE 2

Table 1

Quality control parameter for Wakame Powder

| Description | |
|---|---|
| Color | Green |
| Odor | Fishy |
| OrganolepticTaste | Salty |
| Identification | By Thin Layer Chromatography |
| Amount of fucoxanthin extracted from Wakame Seaweed at 25°C | Not Less Than 10% |
| Fucoxanthin Content By HPLC | Not Less Than 0.5% |
| | |

Table 2

Quality Control Parameters of Wakame Extract

| Description | green powder |
|---|---|
| Identification | by TLC |
| Solubility in Alcohol | not less than 30% |
| pH of w/v suspension | 4 - 7 |
| Loss On Drying (Moisture) | < 7% W/W |
| Ash content | < 10 % w/w |
| Excipient | > 2% |
| Bulk density | 0.6 - 0.9 gm/ml |
| Heavy Metals content | < 20 ppm |
| Arsenic (As) | <1ppm |
| Lead (Pb) | <10ppm |
| Cadmium (Cd) | <0.3ppm |
| Mercury (Hg) | <1.0 ppm |
| Iodine ($I_2$) | <1.0 ppm |
| Total Viable Aerobic Count | <10,000 Cfu/g |
| Total Fungal Count | <100 Cfu/g |
| Total Enterobacteriaceae | <100 Cfu/g |
| E. coli | Negative |
| Salmonella typhii | Negative |
| S. aureus | Negative |
| Fucoxanthins By HPLC | >10.0 % w/w |

PROCESS FOR PRODUCING A STABLE CONCENTRATED DIETARY SUPPLEMENT AND SUPPLEMENT PRODUCED THEREBY

CROSS-REFERENCE TO RELATED APPLICATION

The present application claims benefit of and priority to U.S. Provisional Patent Application Ser. No. 61/049,615 entitled PROCESS FOR PRODUCING A STABLE CONCENTRATED DIETARY SUPPLEMENT AND SUPPLEMENT PRODUCED THEREBY, filed May 1, 2008, the entire contents of which are hereby incorporated by reference herein.

TECHNICAL FIELD

The invention relates to the field of dietary supplements. More particularly, the invention is directed to a process for preparing an improved dietary supplement useful for applications including, but not limited to, weight loss, said supplement containing fucoxanthin as the active ingredient. The invention is directed, as well, as to the product produced by the subject process. Due to the method of its preparation the concentration of the active ingredient contained in the supplement according to the invention is significantly increased while the concentration of undesirable components, such as iodine and/or heavy metals, is correspondingly decreased, in comparison to products previously sold for related uses. Furthermore, supplements produced according to the process described herein possess a substantially enhanced stability (i.e., "shelf life") in contrast to previously available products comprising the same active component.

BACKGROUND

Products containing fucoxanthin have been commercially available as, for example, dietary supplements, for a number of years. Fucoxanthin is a carotenoid commonly found in the pigment of several different seaweeds including, for example, brown seaweed. A carotenoid is one of a group of orange or red plant pigments that include the carotenes. Carotenes occur in several isomeric forms, at least one of which is useful as a dietary supplement due to its nutritional properties.

Previously available fucoxanthin-containing products were not particularly efficacious for use as dietary supplements, however, for a variety of reasons. For example, the percentage assay of the 'active' fucoxanthin in such products was typically less than 2% (by wt.) total fucoxanthin content. This limited amount of active material has been found insufficient, however, to produce the effects such as weight loss desired by those who ingest such products. Additionally, the iodine and heavy metal contents of the previously available commercial products was relatively high. That is, analyses of such prior art products have led to the discovery that both iodine and, e.g., arsenic, were present at unacceptable levels for the product to be considered fit for human consumption.

Further, the above-described 'prior art' products were typically tested by their manufacturers by means of a well-known Ultraviolet-Visible (UV-Vis) analysis method for the presence and/or concentration of the active component. This testing method, however, has subsequently been found not to be the best method for achieving these ends. This is due to the fact that the method is more apt to provide a general indication for the presence of any carotenoid pigment, such as beta-carotene and is thus not capable of specifically monitoring an amount of fucoxanthin present in a sample. The UV-Vis method of testing thus provides unreliable results, which thereby permits the introduction into the marketplace of products which contain no trace of fucoxanthin but which are, nevertheless, alleged by the manufacturer and/or marketer to contain this material as an active component.

Finally, as is well known in this field many of the carotenoids, including fucoxanthin, are relatively unstable. Thus, they are rather readily degradable due, for example, to the influence of environmental factors. This result is antithetical to the requirements of manufacturers and retail outlets which market supplements containing fucoxanthin as an active material which typically require that the active component exhibit a relatively lengthy shelf life of about 2-3 years.

SUMMARY

It is therefore an object of the present invention to provide a method for preparing a dietary supplement product useful in applications including, but not limited to, weight loss, wherein the product comprises as an active component a fucoxanthin-containing material and wherein such product is substantially free of the deficiencies noted above.

It is a further object to provide such a dietary supplement useful in promoting, e.g., weight loss in subjects to whom it is administered, which has a significantly higher concentration of the active fucoxanthin component than was found in previously available commercial products of this type, while concurrently lowering and preferably eliminating entirely the concentration of iodine and heavy metals, such as arsenic, which otherwise may be found therein.

It is a still further object to provide a fucoxanthin-based dietary supplement containing an elevated level of active fucoxanthin component compared to previously available products, which exhibits an enhanced level of stability of the active material such that the product is provided with a 'shelf life' of at least about 2-3 years.

A novel preparation process for forming the improved fucoxanthin-containing product according to the present invention has been developed, wherein such process utilizes as a starting material, freeze-dried flakes of a Japanese wakame seaweed (*Undaria pinnatifida*) product, comprising fucoxanthin, preferably in an amount greater than 0.5% by weight. The seaweed starting material is treated by its supplier (as discussed below) with a proprietary drying and curing process to render the active fucoxanthin component contained therein more readily available in a subsequent extraction process (described below) for separating the active component from the seaweed.

The particle size of the seaweed flakes is initially reduced by converting them into a powder having a substantially homogeneous particle size. After undergoing a Quality Control (QC) analysis, in a next step at least a portion of the active fucoxanthin component is extracted from the powder with use of a solvent extraction technique, by combining a quantity of the powder with an effective amount of a solvent capable of extracting fucoxanthin therefrom to form a mixture, whereby at least a portion of the fucoxanthin contained in the powder material constituting the mixture is extracted into the solvent. If desired the powder may be subjected to multiple extraction treatments, whereupon the various solvent extraction fractions are separated from the solid material, combined and then concentrated via a distillation treatment carried out at a reduced pressure to produce a thick, syrupy mass having a solids content of from about 10 to about 99 wt %. The aim of the concentration step is to achieve an elevated concentration of the active fucoxanthin (i.e., within the syrupy mass), desirably in the area of at least about 5% by weight and more preferably at least about 10% by weight.

The mass is then dissolved, using a quantity of an organic non-polar solvent having a Polarity Index <6, following which the remaining insoluble portion is separated and discarded. The liquid filtrate is then once again concentrated and then, for purposes of Quality Control the concentrated filtrate containing the active fucoxanthin material may be analyzed by various chromatographic methods, including thin-layer chromatography ("TLC") and high pressure liquid chromatography ("HPLC") for the presence of 'contaminants' such as Iodine and/or heavy metals such as arsenic.

Following the quality control analysis, substantially all the remaining solvent is removed, e.g., with the use of a vacuum rotary dryer or other appropriate method and the remaining dried mass is ground and sifted. The resultant product is then analyzed with regard to the parameters set forth in Table 2 contained in FIG. 2.

The product produced as described above contains a significantly higher percentage (by weight) of the fucoxanthin active material, i.e., in the range of at least about 10 wt %, than the previously available commercial products, and also having, conversely, a significantly decreased percentage of iodine and heavy metal content, wherein the product conforms with all required specifications for use as a dietary supplement. Furthermore, analysis of the resultant material has demonstrated that it possesses a significantly enhanced shelf life, i.e., in the area of about 2-3 years, before any significant breakdown of the active component is encountered. The product appears particularly useful in a number of applications including, for example, promoting weight loss.

BRIEF DESCRIPTION OF THE FIGURES

FIG. 1 is a flow chart illustrating various preferred steps of the process described herein; and FIG. 2 includes Table 1, "Quality Control Parameters for Wakame Powder" and Table 2, "Quality Control Parameters for Wakame Extract", referred to in FIG. 1.

DETAILED DESCRIPTION

Both the process of the invention and the improved supplement product thus produced, containing a significantly increased amount (compared to the prior art) of fucoxanthin as an active ingredient (e.g., at least 10-12 wt %) with correspondingly decreased amounts of iodine and heavy metals, are described in further detail below.

As indicated above, in a first stage of the preferred process a starting material comprising a dried wakame seaweed product (*Undaria pinnatifida*) obtained from Riken Vitamin Company, Tokyo, Japan through its subsidiary Riken Vitamin Company USA located in Chicago, Ill., USA is provided. The material is sold under the Trade Name, "*Undaria Pinnatifida* dry flakes". The *Undaria Pinnatifida* dry flakes wakame seaweed material sold by the Riken Company is typically harvested between latitude 35-40 North in the Sea of Japan. The Riken Company produces the dried flakes from the edible wild-crafted wakame seaweed thus obtained with the use of a proprietary drying and curing process. The subject process results in the production of cured dried flakes wherein: (1) the nutritional content found in the original seaweed starting material is maintained, (2) extraction of the active fucoxanthin component is facilitated (at least 10 wt % of fucoxanthin contained in the flakes is soluble in, e.g., ethanol, at 25° C.) and (3) wherein the shelf life of the active material is extended to around 2-3 years without significant degradation.

In a further stage of the preferred preparation process the dried wakame seaweed flakes are subjected to an extraction and concentration treatment summarized, for example, in FIG. 1 submitted herewith.

As described in FIG. 1, in a preferred embodiment the crude wakame flakes obtained from the Riken Company are first ground into a powder with the use of a commercial pulverizer via a methodology which is well-known in this art. The resultant pulverized material then undergoes a quality control (QC) analysis, via preferably a batch analysis process, along the lines set forth in Table 1 of FIG. 2. As shown in the subject Table, the analysis is carried out with the use of TLC and HPLC techniques that are well known in this field of art. The TLC methodology is shown and described in Appendix 1.1 attached at the end of this specification, wherein some representative examples of HPLC analyses of the raw material are described in Appendix 2.1 (as also mentioned in FIG. 2). Once the material receives QC approval, it is passed onward to the extraction stage, as further shown in FIG. 1.

In the preferred embodiment of the extraction stage a portion (preferably weighing about 100 kg) of the pulverized material may be loaded into a commercially available extractor device and the device is then charged with approximately 500 liters of a solvent capable of extracting the fucoxanthin from the powder. The extraction is carried out such that at least a portion of fucoxanthin contained in the powder passes into the solvent. The extraction cycle may be repeated several times, preferably 5×, to ensure substantially complete extraction of the fucoxanthin active component from the pulverized flake material. Following completion of the extraction, the solvent phase is separated from any powder that is not dissolved and the liquid filtrate is then transferred to a commercially available distillation apparatus.

The next step in the preferred process constitutes a distillation step wherein distillation of the solvent phase is carried out under reduced pressure at a temperature below about 50° C. to obtain a thick, syrupy mass having a solids content in the range of from about 10 to about 99 wt %.

The resultant mass is then combined with a sufficient amount of an organic non-polar solvent having a Polarity Index <6, wherein the solvent is able to substantially dissolve the mass to form a solvent solution thereof. The solvent solution is thereafter purified by filtering out any insoluble material, which insoluble material is then discarded.

The organic non-polar solvent is then distilled off under reduced pressure and the remaining solid is dried, e.g., in a vacuum rotary drier at a temperature below about 50° C., after which the remaining solid product is ground and sifted to remove any agglomerated material.

Upon completion of the steps described above, the ground material is analyzed for quality control purposes with the use of TLC and HPLC in accordance with the parameters set forth in Table 2 of FIG. 2. The HPLC technique utilized for this analytical step is described in the additional attachment found at the end of this specification entitled, "Determination of Fucoxanthin in fucopure (Wakame Extract)".

In one preferred embodiment, the powder formed by grinding the crude wakame seaweed flakes measures from about 10 to about 20 mesh in size.

In another preferred embodiment, the extraction solvent used in extracting fucoxanthin from the powder is an organic solvent capable of extracting at least 5 wt % of fucoxanthin from the powder. The powder/solvent mixture may undergo a plurality (e.g., 5) of solvent extractions, whereupon the various extraction fractions are all combined for further treatment as described herein. In another preferred embodiment, the organic extraction solvent is an aliphatic or aromatic class of organic solvent. In a further preferred embodiment, the aliphatic alcohol is selected from the group consisting of ethanol, methanol, isopropyl alcohol, ethylene dichloride, methylene dichloride and the like. In still another preferred embodiment the fucoxanthin is extracted from the mixture of solvent and powder in an amount of at least about 10% by weight. In a more preferred embodiment, the extraction may be carried out at approximately 10-70° C. for up to about three hours in a substantially continuous solvent flow.

In another preferred embodiment the solvent containing the extracted fucoxanthin is separated from the extracted powder material via a filtration process, which process would be well known among those working in this art.

In a further preferred embodiment the distillation step takes place at a reduced pressure of from about 0.20 kg/sq. cm to about 0.8 kg/sq. cm.

In another preferred embodiment the fucoxanthin-containing syrupy mass has a solids content of from about 30 to about 45% by weight.

In an additional preferred embodiment the non-polar solvent used in the purification treatment stage is selected from the group consisting of butanol, chloroform, ethyl acetate and hexane.

A further preferred embodiment constitutes the formation of a fucoxanthin-containing dietary supplement product produced according to the method disclosed and claimed herein, said supplement containing less than about 1 ppm iodine and less than about 1 ppm arsenic and wherein the fucoxanthin contained in the supplement remains substantially stable for at least about 2 years.

In another preferred embodiment, a variety of dosage forms, including for example, tablets, capsules, powders and granules may be produced from the fucoxanthin material produced according to the above-described process.

While the invention has been described in considerable detail with reference to certain specific and preferred versions thereof, it is capable of a variety of further modifications without departing from the spirit and scope of the invention. This application is intended to cover all variations, uses and adaptations of the invention as may be deemed practicable.

What is claimed is:

1. A process for producing a fucoxanthin-containing dietary supplement from *Undaria pinnatifida*, said process comprising:
   (a) providing freeze-dried flakes of *Undaria pinnatifida* containing fucoxanthin, said flakes having a range of particle sizes;
   (b) reducing the particle sizes of said flakes by converting them into a powder having a substantially homogeneous particle size;
   (c) forming a mixture by combining a quantity of said powder with an effective amount of a solvent capable of extracting fucoxanthin from said powder, whereby at least a portion of fucoxanthin contained in said powder is extracted into the solvent;
   (d) separating the solvent containing the extracted fucoxanthin from said mixture;
   (e) subjecting the fucoxanthin-containing solvent to a distillation under a reduced pressure to remove at least a portion of said solvent, thus forming a syrupy fucoxanthin-containing mass having a solids content of from about 10 to about 99% by weight;
   (f) combining said fucoxanthin containing mass with a sufficient amount of an organic non-polar solvent having a Polarity Index <6, wherein the organic non-polar solvent is able to substantially dissolve the mass and form a solvent solution containing said fucoxanthin, and whereupon the solvent solution is purified by filtering out any remaining insoluble material which does not go into said solvent solution and discarding said insoluble material from the solvent solution;
   (g) concentrating said solvent solution by removing substantially all of said solvent to produce a dried mass containing fucoxanthin; and
   (h) grinding and sifting the dried mass containing fucoxanthin to obtain particles measuring approximately 60-100 mesh in size, said particles containing at least 10% by weight of fucoxanthin.

2. The process of claim 1, wherein in step (b) said flakes of the wakame seaweed are ground with a pulverizer to form said powder.

3. The process of claim 1, wherein the solvent in step (c) is an organic solvent and wherein the mixture may undergo a plurality of extraction treatments wherein fucoxanthin is extracted from said mixture.

4. The process of claim 3, wherein the organic extraction solvent is an aliphatic or an aromatic organic solvent.

5. The process of claim 4, wherein the organic solvent is selected from the group consisting of ethanol, methanol, isopropyl alcohol, ethylene dichloride and methylene dichloride.

6. The process of claim 3, wherein the extraction is carried out at approximately 10° C. -70° C. for approximately 3 hours in the presence of a continuously circulating solvent flow.

7. The process of claim 1, wherein the solvent in step (d) is separated from said mixture by filtration.

8. The process of claim 1, wherein the distillation in step (e) takes place within a pressure range of from about 0.20 kg/sq. cm to about 0.8 kg/sq. cm.

9. The process of claim 1, wherein the syrupy fucoxanthin-containing mass produced according to step (e) has a solids content of from about 30% to about 45% by weight.

10. The process of claim 1, wherein the distillation step (e) is carried out at a pressure of from about 0.20 kg/sq. to about 0.8 kg/sq.

11. The process of claim 1, wherein the organic non-polar solvent in step (f) is selected from the group consisting of butanol, chloroform, ethyl acetate and hexane.

12. The process of claim 1, wherein the filtered solvent solution produced in step (f) is dried in a vacuum rotary dryer at a temperature below about 50° C.

* * * * *